US00PP19937P2

(12) United States Plant Patent
Trees

(10) Patent No.: US PP19,937 P2
(45) Date of Patent: Apr. 21, 2009

(54) ***VERBENA* PLANT NAMED 'BALAZDARE'**

(50) Latin Name: *Verbena×hybrida*
Varietal Denomination: Balazdare

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/895,119

(22) Filed: Aug. 23, 2007

(51) Int. Cl.
*A01H 5/00* (2006.01)

(52) U.S. Cl. ..... Plt./308
(58) Field of Classification Search ..... Plt./308
See application file for complete search history.

(56) References Cited

U.S. PATENT DOCUMENTS

PP16,667 P2 * 6/2006 Trees ..... Plt./308
PP17,630 P2 * 4/2007 Trees ..... Plt./308

OTHER PUBLICATIONS

UPOV ROM GTTIM Computer Database, GIT Jouve Retreival Software 2008/02 Citaiton for 'Balazdare'.*
Canada Plant Breeders' Rights application No. 07–5882 filed Apr. 12, 2007.

* cited by examiner

*Primary Examiner*—Wendy C. Haas
(74) *Attorney, Agent, or Firm*—Audrey Charles

(57) ABSTRACT

A new and distinct cultivar of *Verbena* plant named 'Balazdare', characterized by its dark red-colored flowers, dark green-colored foliage, and moderately vigorous, and trailing, spreading growth habit.

1 Drawing Sheet

Latin name of genus and species of plant claimed: *Verbena×hybrida.*
Variety denomination: 'Balazdare'.

BACKGROUND OF THE INVENTION

The present invention relates to a new and distinct cultivar of *Verbena* plant botanically known as *Verbena×hybrida* and hereinafter referred to by the cultivar name 'Balazdare'.

The new cultivar originated in a controlled breeding program in Arroyo Grande, Calif. August 2004. The objective of the breeding program was the development of *Verbena* cultivars that are freely flowering with large full inflorescences, attractive leaf and flower coloration, and a trailing, spreading growth habit.

The new *Verbena* cultivar is the result of cross-pollination. The female (seed) parent of the new cultivar is the proprietary *Verbena×hybrida* breeding selection designated BFP 2465AA, not patented, characterized by its dark red-colored flowers, dark green-colored foliage, and vigorous, trailing growth habit. The male (pollen) parent of the new cultivar is AZTEC Red Velvet 'Balazreve', U.S. Plant Pat. No. 16,667, characterized by its dark scarlet red-colored flowers, dark green-colored foliage, and mounded and trailing growth habit. The new cultivar was discovered and selected as a single flowering plant within the progeny of the above stated cross-pollination during January 2005 in a controlled environment at Arroyo Grande, Calif.

Asexual reproduction of the new cultivar by terminal stem cuttings since January 2005 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balazdare' as a new and distinct cultivar of *Verbena* plant:

1. Dark red-colored flowers;
2. Dark green-colored foliage; and
3. Moderately vigorous, and trailing, spreading growth habit.

Plants of the new cultivar differ from plants of the female parent primarily in growth habit and vigorousness and from plants of the male parent primarily in flower color. Plants of the new cultivar have dark red-colored flowers whereas plants of the male parent have dark scarlet red colored flowers.

Of the many commercially available *Verbena* cultivars known to the inventor, the most similar in comparison to the new cultivar is the male parent AZTEC Red Velvet 'Balazreve', U.S. Plant Pat. No. 16,667. However, in side by side comparisons, plants of the new cultivar differ from plants of 'Balazreve' in the following characteristics:

1. Plants of the new cultivar have a flower color different from plants of 'Balazreve'; and
2. Plants of the new cultivar have a corolla tube whisker color different from plants of 'Balazreve'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balazdare'. The plants were grown in 4.5 inch pots for 7 weeks in a greenhouse at West Chicago, Ill. Plants were given one pinch at transplant.

DETAILED BOTANICAL DESCRIPTION

Figure 1:
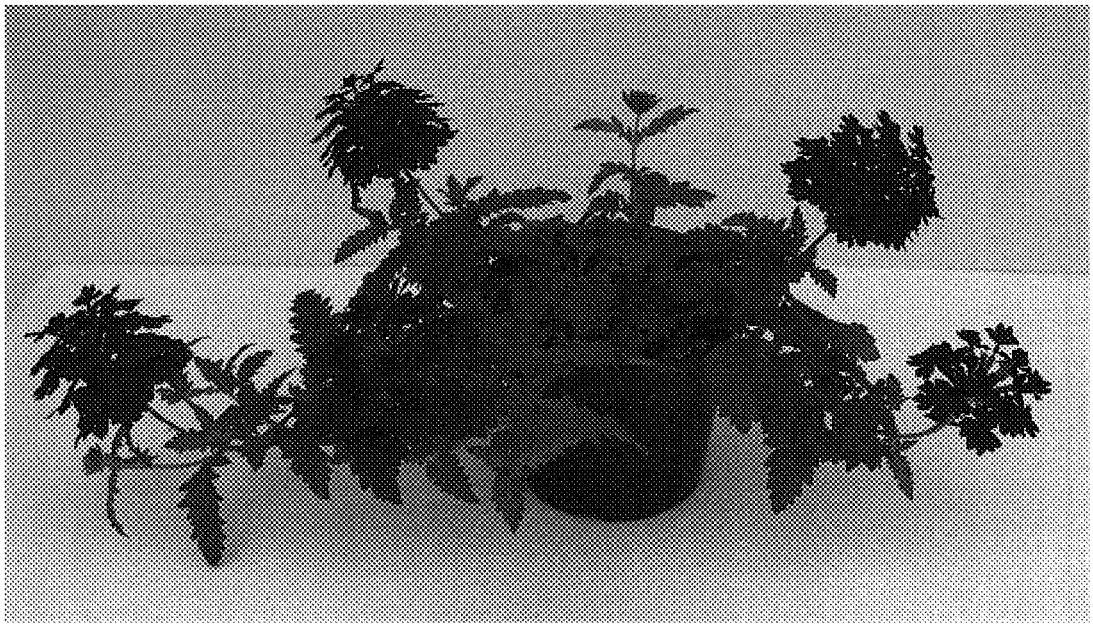
FIG. 1 illustrates a side view of the overall growth and flowering habit of 'Balazdare'.
Figure 2:
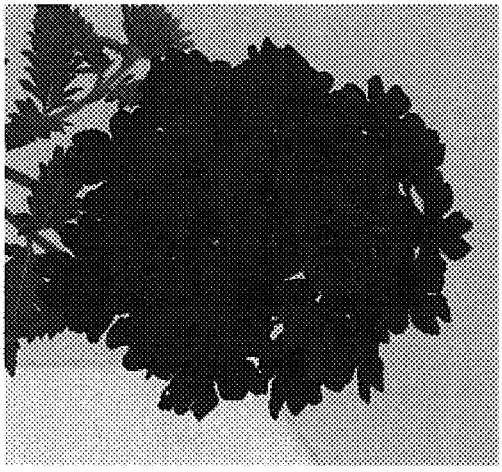
FIG. 2 illustrates a close-up view of an individual inflorescence of 'Balazdare'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 7, 2007 between 9:00 a.m. and 11:00 a.m. under natural light conditions in West Chicago, Ill..

The following descriptions and measurements describe plants produced from cuttings taken from stock plants and grown in a glass-covered greenhouse under conditions comparable to those used in commercial practice. The plants were grown at West Chicago, Ill. 4.5 inch pots for 7 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Verbena×hybrida* cultivar Balazdare.

Parentage:

*Female parent.*—Proprietary *Verbena×hybrida* breeding selection designated BFP 2465AA, not patented.

*Male parent.*—AZTEC Red Velvet. 'Balazreve', U.S. Plant Patent No. 16,667.

Propagation:

*Type cutting.*—Terminal stem.

*Time to initiate roots.*—Approximately 6 to 9 days.

*Time to produce a rooted cutting.*—Approximately 24 to 28 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, and trailing, spreading.

*Size.*—Height from soil level to top of plant plane: Approximately 9.9 cm. Width: Approximately 35.3 cm.

*Branching habit.*—Freely branching, pinching enhances basal branching. Quantity of main branches per plant: Approximately 5.

*Branch.*—Shape: Square in cross section. Strength: Strong. Length: Approximately 19.7 cm. Diameter: Approximately 3.0 mm. Length of central internode: Approximately 1.9 cm. Texture: Densely pubescent with a mixture of glandular and nonglandular hairs. Gland color: Colorless, transparent. Color of young and mature stems: 144A.

Foliage description:

*General description.*—Quantity of leaves per main branch: Approximately 12. Fragrance: None. Form: Simple. Arrangement: Opposite.

*Leaves.*—Aspect: Perpendicular to stem. Shape: Ovate. Margin: Serrate. Apex: Acute. Base: Truncate. Venation pattern: Pinnate. Length of mature leaf: Approximately 5.3 cm. Width of mature leaf: Approximately 3.3 cm. Texture of upper surface: Sparsely pubescent. Texture of lower surface: Densely pubescent on venation with a mixture of glandular and nonglandular hairs. Gland color: Colorless, transparent. Color of upper surface of young foliage: 139A with venation of 144D. Color of lower surface of young and mature foliage: 138B with venation of 145C. Color of upper surface of mature foliage: Darker than 137A with venation of 144D.

*Petiole.*—Length: Approximately 5.0 mm. Diameter: Approximately 2.0 mm. Texture: Densely pubescent. Color: 144D.

Flowering description:

*Flowering habit.*—'Balazdare' is freely flowering under outdoor growing conditions with substantially continuous blooming from spring through autumn and year-round in greenhouse environment.

*Lastingness of individual flower on the plant.*—Approximately 5 to 7 days.

Inflorescence description:

*General description.*—Type: Corymb. Shape: Hemispherical. Quantity per plant: Approximately 6. Fragrance: None. Length or height: Approximately 5.4 cm. Width: Approximately 6.3 cm. Quantity of fully open flowers per inflorescence: Approximately 27.

*Peduncle.*—Strength: Strong. Aspect: Erect. Length: Approximately 3.5 cm. Diameter: Approximately 2.0 mm. Texture: Densely pubescent on venation with a mixture of glandular and nonglandular hairs. Gland color: Closest to 187A. Color: 144A.

Flower description:

*General description.*—Type: Sessile, salverform.

*Bud.*—Rate of opening: Generally takes 2 to 3 days for bud to progress from first color to fully open flower. Quantity unopened inflorescences per plant: Approximately 3.

*Bud just before opening.*—Shape: Elongated, globular at apex. Length: Approximately 1.7 cm. Diameter: Approximately 3.2 mm. Color: 53A.

*Corolla.*—Shape: Round. Diameter: Approximately 2.3 cm. Depth: Approximately 2.7 cm.

*Petals.*—Quantity: 5, fused at base forming a tube. Shape: Obovate. Appearance: Velvety. Margin: Entire. Apex: Emarginate. Length of upper petal from tube: Approximately 1.1 cm. Width of upper petal: Approximately 9.2 mm. Length of lateral petals from tube: Approximately 1.0 cm. Width of lateral petals: Approximately 7.0 mm. Length of lower petals from tube: Approximately 1.0 cm. Width of lower petals: Approximately 6.0 mm. Texture of upper surface: Glabrous. Texture of lower surface: Sparsely pubescent with a mixture of glandular and nonglandular hairs. Gland color: Colorless, transparent. Color of upper surface when fully open: 46A darkening in center of flower to 53A. Color of lower surface when fully open: 53B. Whisker color surrounding the opening of the corolla tube: 64A.

*Corolla tube.*—Length: Approximately 2.2 cm. Diameter at distal end: Approximately 2.0 mm. Diameter at proximal end: Approximately 1.0 mm. Texture of inner and outer surfaces: Densely pubescent. Color of inner surface: 145D at proximal end transitioning to 145B at distal end. Color of outer surface: 145D with a faint overlay of 64D at distal end.

*Calyx.*—Shape: Tubular with 5 acute tips. Length: Approximately 1.5 cm. Width: Approximately 2.0 mm.

*Sepals.*—Quantity per flower: 5, fused at base. Shape: Linear. Apex: Acute. Length: Approximately 1.5 cm. Width: Approximately 1.0 mm., Texture of inner surface: Densely pubescent. Texture of outer surface: Densely pubescent on venation with a mixture of glandular and nonglandular hairs. Gland color: Mixture of colorless, transparent and closest to 187A, transparent. Color of inner and outer surfaces: 137A, transparent where margins fuse. Stipule shape: Lanceolate. Stipule apex: Acute. Stipule length: Approximately 7.0 mm. Stipule width at base: Approximately 2.0 mm. Stipule texture: Densely pubescent with a mixture of glandular and nonglandular hairs. Stipule gland color: Colorless. Stipule color: 144A at base transitioning to 137A at apex.

*Reproductive organs.*—Androecium: Stamen quantity: 4, didynamous. Stamen length: Approximately 3.0 mm. Stamen length of shorter pair: Approximately 2.0 mm. Anther shape: Bilobed, ovoid. Anther length: Approximately 1.0 mm. Anther color: 154B. Pollen amount: Sparse. Pollen color: 154D. Gynoecium: Pistil quantity: 1 per flower. Pistil length: Approximately 2.0 cm. Stigma shape: Biparted. Stigma length: Less than 1 mm. Stigma color: 143A. Style length: Approximately 1.9 cm. Style color: 144C transitioning to 144D at base. Ovary diameter: Approximately 1.0 mm. Ovary texture: Glabrous. Ovary color: N144C.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balazdare', substantially as herein shown and described.

* * * * *